United States Patent [19]

Tucker et al.

[11] Patent Number: 5,110,735
[45] Date of Patent: May 5, 1992

[54] THERMOSTABLE PURIFIED ENDOGLUCANASE FROM THERMOPHILIC BACTERIUM ACIDOTHERMUS CELLULOLYTICUS

[75] Inventors: Melvin P. Tucker, Lakewood; Karel Grohmann; Michael E. Himmel, both of Littleton; Ali Mohagheghi, Golden, all of Colo.

[73] Assignee: Midwest Research Institute, Kansas City, Mo.

[21] Appl. No.: 412,434

[22] Filed: Sep. 26, 1989

[51] Int. Cl.$^5$ .......................... C12N 9/42; C12N 1/00
[52] U.S. Cl. ........................................ 435/209; 435/822
[58] Field of Search ..................... 435/209, 252.1, 822, 435/101, 183

[56] References Cited

U.S. PATENT DOCUMENTS

| | | | |
|---|---|---|---|
| 3,398,055 | 8/1968 | Bruno | 435/911 |
| 4,081,328 | 3/1978 | Skinner et al. | 435/911 |
| 4,610,965 | 9/1986 | Johnson et al. | 435/234 |

OTHER PUBLICATIONS

Amelunxen et al., *Mechanisms of Thermophily*, Crit. Rev. Microbiol., 6, pp. 343–393, 1978.
Saddler et al., *Cellulolytic enzyme System of Acetivibrio, Cellulolyticus,* Can. J. Microbiol, vol. 27, pp. 288–294, 1981.
Mandels, M. and J. Weber, 1969 "*Production of Celluloses*", Advan. Chem. Ser. 95, pp. 391–414.
Mohagheghi et al., 1986, "Isolation and Characterization of a Cellolyticius", Gen. Nov. Sp. Nov. A Genius of Thermophilic Acidophilic Celluloytic Bacterium, Int. J., Syst. Baceeriol 36, pp. 435–443.

*Primary Examiner*—Douglas W. Robinson
*Assistant Examiner*—Michael V. Meller
*Attorney, Agent, or Firm*—Ken Richardson

[57] ABSTRACT

A substantially purified high molecular weight cellulase enzyme having a molecular weight of between about 156,000 to about 203,400 daltons isolated from the bacterium *Acidothermus cellulolyticus* (ATCC 43068) and a method of producing it are disclosed. The enzyme is water soluble, possesses both $C_1$ and $C_x$ types of enzymatic activity, has a high degree of stability toward heat and exhibits both a high optimum temperature activity and high inactivation characteristics.

4 Claims, 5 Drawing Sheets

THERMOSTABLE PURIFIED ENDOGLUCANASE FROM THERMOPHILIC BACTERIUM ACIDOTHERMUS CELLULOLYTICUS

CONTRACT ORIGIN OF THE INVENTION

The United States Government has rights in this invention pursuant to contract No. DE AC02-83CH10093 between the United states Department of Energy and the Midwest Research Institute.

BACKGROUND OF THE INVENTION

1. Field of the Invention

The invention relates generally to a purification process for *Acidothermus cellulolyticus* endoglucanases, and pertains more specifically to a purification protocol used to purify the high and two low molecular weight endoglucanases from the cellulase enzyme complex obtained from *Acidothermus cellulolyticus* bacterium, which has been submitted to the American Type Culture Collection (ATCC) under collection number 43068.

2. Description of the Prior Art

Cellulose consists of long insoluble chains of covalently bonded glucose molecules, and in this condition, these long insoluble chains are too large to be transported through human and animal cell walls. However, through the agency of microorganisms, such as fungi and bacteria, enzymes known as cellulases are secreted, and these enzymes hydrolyze or depolymerize the cellulose into its monomeric component of glucose, which is a sugar that can be readily transported through the cell wall and metabolized.

Cellulases are enzyme complexes that include three different types of enzymes. These enzymes are endoglucanase, exoglucanase and a cellobiase, and the synergistic action of these three enzymes are necessary to completely depolymerize cellulose into glucose.

The synergistic reaction occurs as a result of a sequential, cooperative action between the three enzyme components in a complex in which the product of one enzyme reaction becomes the substrate for the next enzyme.

While many microorganisms have been classified as cellulolytic, only a few possess a complete cellulase complex capable of efficient deploymerization of crystalline cellulose under certain conditions. *Trichoderma reesei* (Simmons, E.G., 1977. Abst, Ind Mycol. Cong., p. 618), Which is a common soil fungus of the Deuteromycete family, is one such cellulolytic microorganism; however, the percent maximum activity per (mM) of cellobiase is too limited and this cellulase is not highly stable when exposed to high temperature ranges. Although the enzymes of the organism *Trichoderma reesei* have been subjected to intensive biochemical study (Shoemaker, S.P. and R.D., Brown, 1978. Enzymic activities of endo-1 4-$\beta$-D Glucanases EC-3.2.1.4 purified from T. viride. Biochim, Biophys. Acta. 523,1, pp. 133-146.), they have not been shown to be stable in the presence of high temperatures. For example, a wild type of *Trichoderma reesei* is known to secrete cellulase enzymes with optimal temperatures of 45° C. for total activity, 55° C. for endoglucanase activity, and after about one hour at 60° C., the cellulase from this *Trichoderma reesei* looses half of its total activity. Cellulases produced by various organisms have been described in U.S. Pat. Nos. 3,232,832 (Rhizophus), 3,398,055 (Trichoderma viride ATCC 16425; and other fungi); 3,438,864 (Eumyees mold organism ATCC 16425, 3,677,899 (Lampteromyces or Formitopsis); and 3,734,831. However, cellulase preparations from Trichoderma viride, while known to be higher in $C_l$ enzyme activity than other commercially available cellulases, have the drawback that optimum temperature for their enzymic reactions is about 50° C. (Mandels, et al. "Cellulases and Their Applications", ACS. Vol. 95, pp 398-411 (1969)).

U.S. Pat. No. 4,081,328 discloses a thermostable cellulase exhibiting both $C_l$ and $C_x$ types of cellylytic activities produced by the fungal organism *Thiolavia terestris* (NRRL 8126). The thermostable cellulase preparation exhibits $C_l$ and $C_x$ cellylytic activities at temperatures from about 60° to about 70° C. (140° to 160° F.).

At present, mesophilic cellulases with temperature optima near 45° to 50° C. from Trichoderma species (Mandels and Weber, 1969. "Production of Cellulases", Advan. Chem. Ser., Vol. 95, pp. 391-414), are used industrially, however, industrial use of mesophilic cellulases require expensive refrigeration to cool the process stream and the chances of contamination by opportunistic microorganisms are greatly increased.

Therefore, a need exist to provide a higher optimum temperature range cellulase enzyme that is capable of replacing the lower optimum temperature (60° to 70° C.) mesophilic cellulase enzymes.

SUMMARY OF THE INVENTION

In accordance with a first aspect of the invention, it has been found that the higher optimum temperature (70° to 80° C.) cellulase enzyme complex from the bacterium *Acidothermus cellulolyticus* produced by the process of the invention can be used to replace the mesophilic cellulase enzymes that are currently used industrially.

The invention process for the preparation of the high optimum temperature cellulase enzymes provides means for concentrating the culture broth of *Acidothermus cellulolyticus* by using ammonium sulfate precipitation (between 40 to 60% saturated solutions) or by ultrafiltration using an Amicon ultrafiltration apparatus equipped with PM-lo membranes and the concentrate can be stored at −20° C. in the presence of 20% glycerol for periods greater than a year with no loss in enzyme activity.

In accordance with the second aspect of the invention, the cellulase enzyme complexes produced by *Acidothermus cellulolyticus* possesses both $C_1$ and $C_x$ enzyme activitity, and exhibit cellulolytic activity at temperatures ranging from 20 to 110° C. and at pH's ranging from 2 to 9, preferably at pH's from about 4 to about 8; and most preferably at a pH of about 5.

An important aspect of the cellulase of the invention is the thermotolerant characteristics where the enzyme exhibits a high stability upon exposure to heat. After incubating the crude enzyme solution for about two hours at 90° C., 20% of enzyme activity still remains intact.

The invention is further directed to the purification and characterization of three thermostable endoglucanases produce by the thermophilic bacterium *Acidothermus cellulolyticus*. The high molecular weight endoglucanase appears to be less table with a temperature optimum near 65° C., while of the two low molecular weight endoglucanases, Endo 1 has a temperature optimum near 80° C.

DETAILED DESCRIPTION OF THE PREFERRED EMBODIMENTS

*Acidothermus cellulolyticus* has been studied in detail taxonomically resulting in both a new genus and species name to support the criteria for novelty of the organism and the cellulase secreted by this organism into the medium in which it has been grown. The detailed characteristics of the organism is published in the International Journal of Systematic Bacterioloy, 36, 1986 pp. 435-443. The microorganism utilizes a wide variety of simple sugars, as Well as a variety of cellulosic materials such as cellulose powder, as the sole carbon source. A minimal mineral media containing inexpensive and readily obtainable salts and a nitrogen source (inorganic ammonium salts or organic nitrogenous materials such as amino acids) is used. Yeast extract may be used by supplementation into the minimal mineral media to serve as a source of various growth factors.

This bacterium grows within a pH range of 3 to 7 and a temperature range of 40° to 70° C. with the optimum growth conditions near pH 5 and a temperature of 55° C.

Stock cultures of *Acidothermus cellulolyticus* are stored at about −70° C. with the addition of dimethylsulfoxide (DMSO) to the primary culture broth. For the cultivation of *Acidothermus cellulolyticus* for the production of cellulase, primary culture inocula are started by thawing the frozen cultures that have been stored and transferring them to flasks containing sterile culture media. The primary culture inocula are used to start the inocula for larger fermenters with the volume of the inocula equal to one tenth the volume of the fermenters to be inoculated. The initial PH of the culture media is about 5.2 and the incubation temperature is set to 55° C. This microorganism reaches maximum growth in about 20 to about 36 hours after which secretion of the cellulase enzyme complex is found to occur.

Crude culture broths from this bacterium show optimal temperature for the depolymerization of crystalline cellulose 75° C., and 83° C. is found for endoglucanase carboxymethyl cellulose (CMC) activity. At 90° C., 38% of optimal activity for degradation of cellulose is found, and 60% of endoglucanase activity is found under standard assay conditions. This cellulase enzyme can replace the mesophilic cellulase enzymes used industrially since its optimum temperature is between 70° to 80° C., above the 60° to 70° (140° to 160° F.) pasteurization range currently used by industry.

EXAMPLE 1

Stock cultures of *Acidothermus cellulolyticus* were maintained at −70° C. by the addition of 77 microliters of DMSO to 1 ml of culture grown to early stationary phase. One milliliter of stock culture was thawed and transferred to a 50 ml shake flask containing 20 ml medium With the compostion shown in Table 1. The flask is incubated at 55° C. for 20 to 36 hours and the culture transferred to a 500 ml flask containing 200 ml of culture media.

Figure 1:
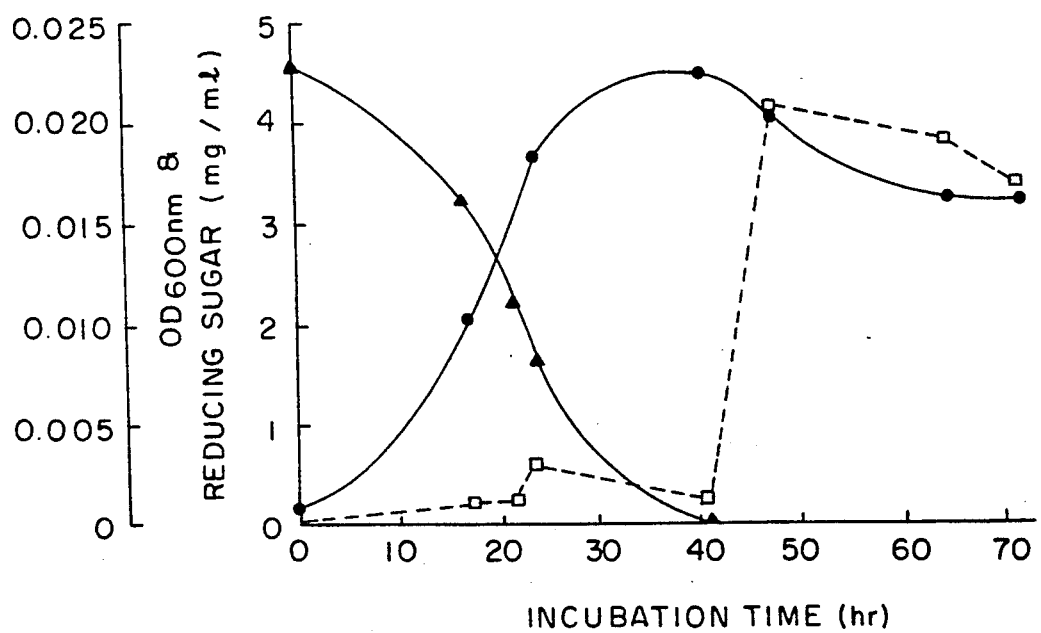
FIG. 1 depicts the growth cycle of *Acidothermus cellulolyticus* grown on 5 (g/l) cellobiase in a 5 l. stirred tank reactor at 55° C. at a pH of about 5.2.

This flask is used as the inoculum to a 5-liter fermenter with a working volume of 2 liters. The pH is controlled at 5.2 by titration with KOH (1N) or HCl (1N). The enzyme activities are measured over 48 hours of this fermentation cycle. One ml samples are taken and centrifuged at 12,000xg with 0.5 ml of the supernatant being used to measure the filter paper (FP) activity in accordance to the method recommended by the International Union of pure and Applied Chemistry (IUpAC), 1987, and the same is incorporated herein by reference in its entirety. In this method 0.5 ml of the supernatant is mixed with 0.75 ml citrate buffer (0.1 M), pH 4.8, to which 0.25 ml of deionized (DI) water is added to bring the total volume in the assay mixture to 1.5 ml. The assay tubes containing 50 mg strips of Whatman #1 filter paper are preincubated at 55° C. before the addition of the enzyme solution, followed by incubation at 55° C. for one hour. The reducing sugar released by the action of the enzyme is measured using the 3,5-dinitrosalicylic acid (DNS) reagent and method. A standard curve by which to compare the glucose released is constructed using accurately weighed glucose standards within the range of 0 to 5 mg. The amount of enzyme added was adjusted to give a total release of glucose at the end of a one hour incubation period equal to 2 mg. The total activity obtained during the course of the fermentation is 0.02 international filter paper units per ml (IFPU/ml). This low value for enzyme activity is natural with many Wild type organisms. Strain improvements are required to increase the cellulase enzyme titer and total productivity. The growth cycle is shown in FIG. 1.

TABLE 1

Media Composition for Growing *Acidothermus cellulolyticus*

| Component | g/L in deionized water |
|---|---|
| $NH_4Cl$ | 2.0 |
| $NH_2PO_4$ | 2.0 |
| $Na_2HPO4$ | 0.2 |
| $MgSO_4 7H_2O$ | 0.4 |
| $CaCl_2$ | 0.04 |
| Yeast Extract | 1.0 |
| Carbon source | 5.0 |
| $FeSO_4$ | 0.01 |
| pH adjusted to 5.2 | |

EXAMPLE 2

The 120 liter fermenter broth is centrifuged using a CEPA type 41 continuous centrifuge followed by concentration of the supernatant using an Amicon DC-30 ultrafiltration apparatus equipped with pM-lo hollow fiber filters to a level of 2 IFPU/ml. The concentrated enzyme solution is mixed with 20% glycerol and stored frozen at −20° C.

EXAMPLE 3

Figure 2:
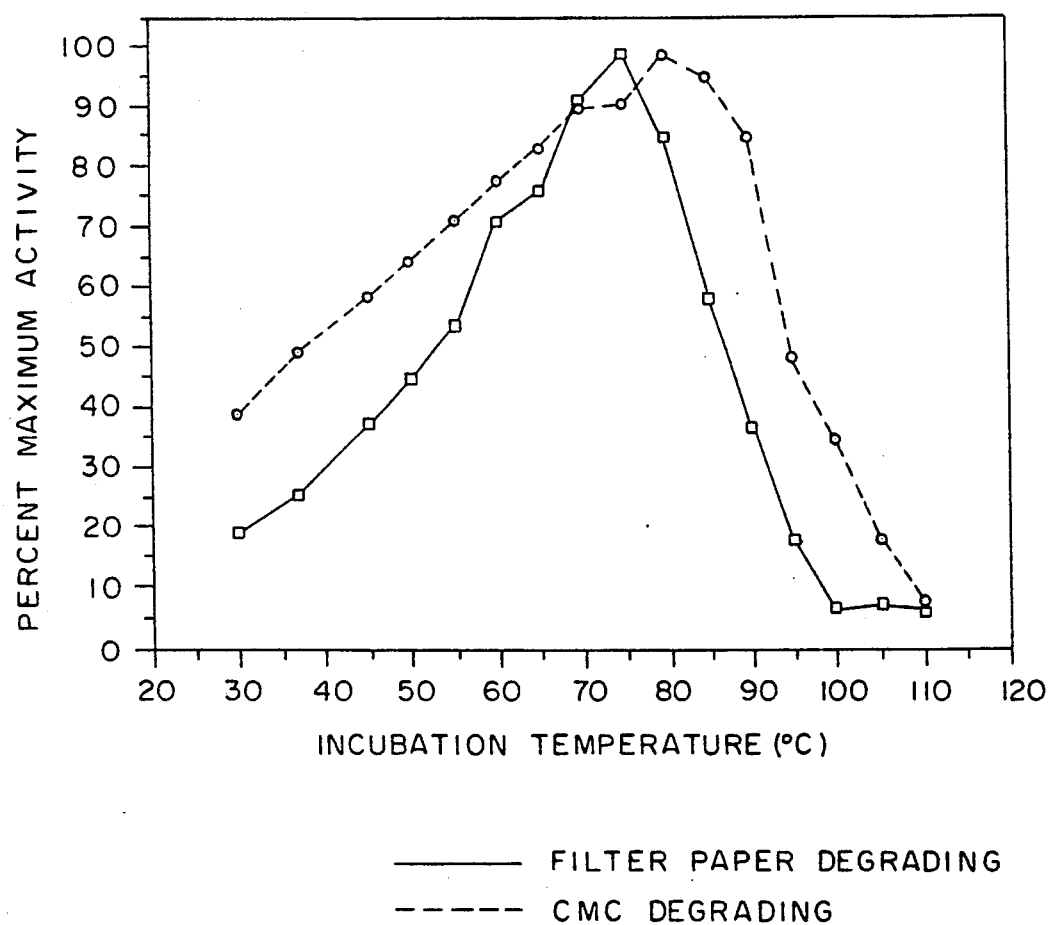
FIG. 2 depicts the activity temperature profile for the crude enzyme from *A. cellulolyticus*.

The temperature range over which the enzymes secreted by *Acidothermus cellulolyticus* is examined and the results are depicted in FIG. 2. The temperature range for filter paper (FP) as well as the measured endoglucanase (CMC) activity is shown over the range of 30° to 110° C. The activities are measured according to the IUPAC methodology published in the reference given in Example 1. The broad temperature range over which the enzymes have significant activity is clearly evident. The temperature optimum at pH 5.0 for filter paper actively is near 75° C. and the endoglucanase activity near 83° C.

EXAMPLE 4

Figure 3:
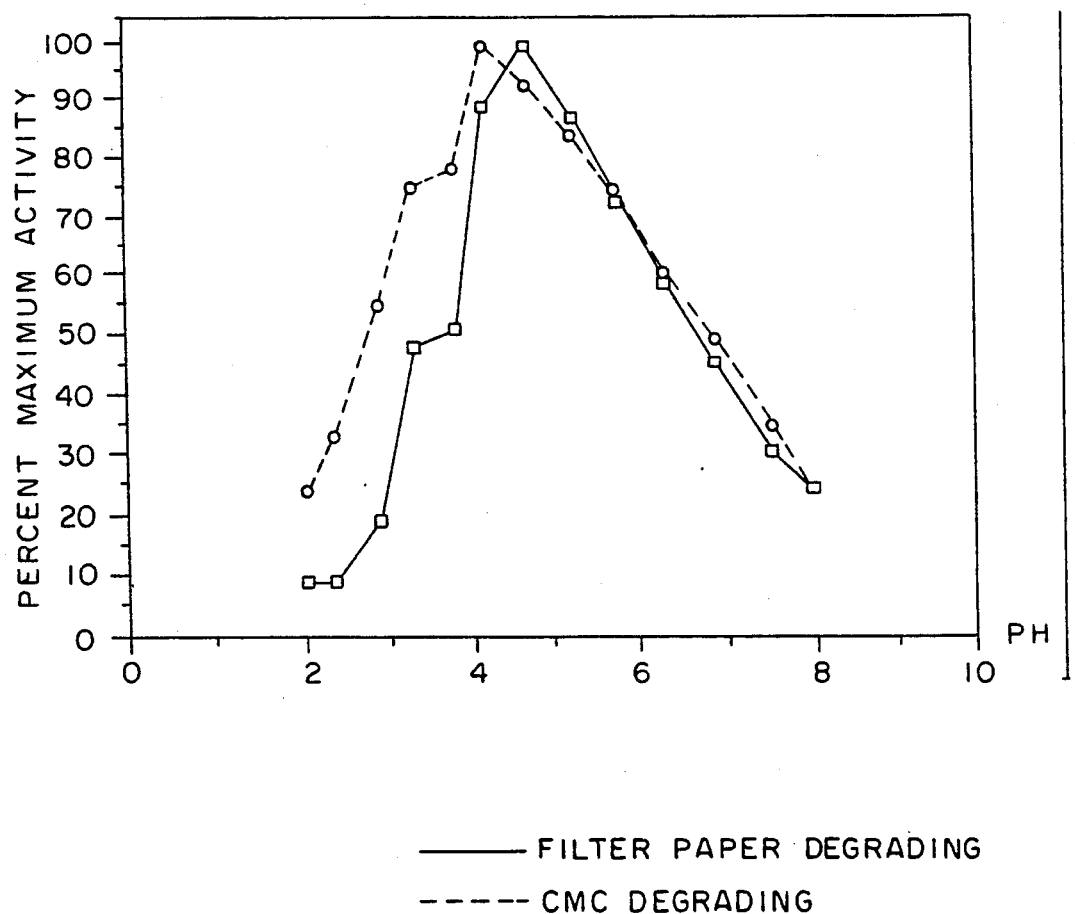
FIG. 3 depicts the activity incubation pH profile for the crude enzyme from *A. cellulolyticus*.

The pH range over which the enzymes secreted by *Acidothermus cellulolyticus* are active is shown in FIG. 3. Filter paper (FP) activity and endoglucanase (CMC) activity is measured over the range of about 2.2 to about 8 using a constant ionic strength buffer system at about 65° C.

EXAMPLE 5

Figure 4:
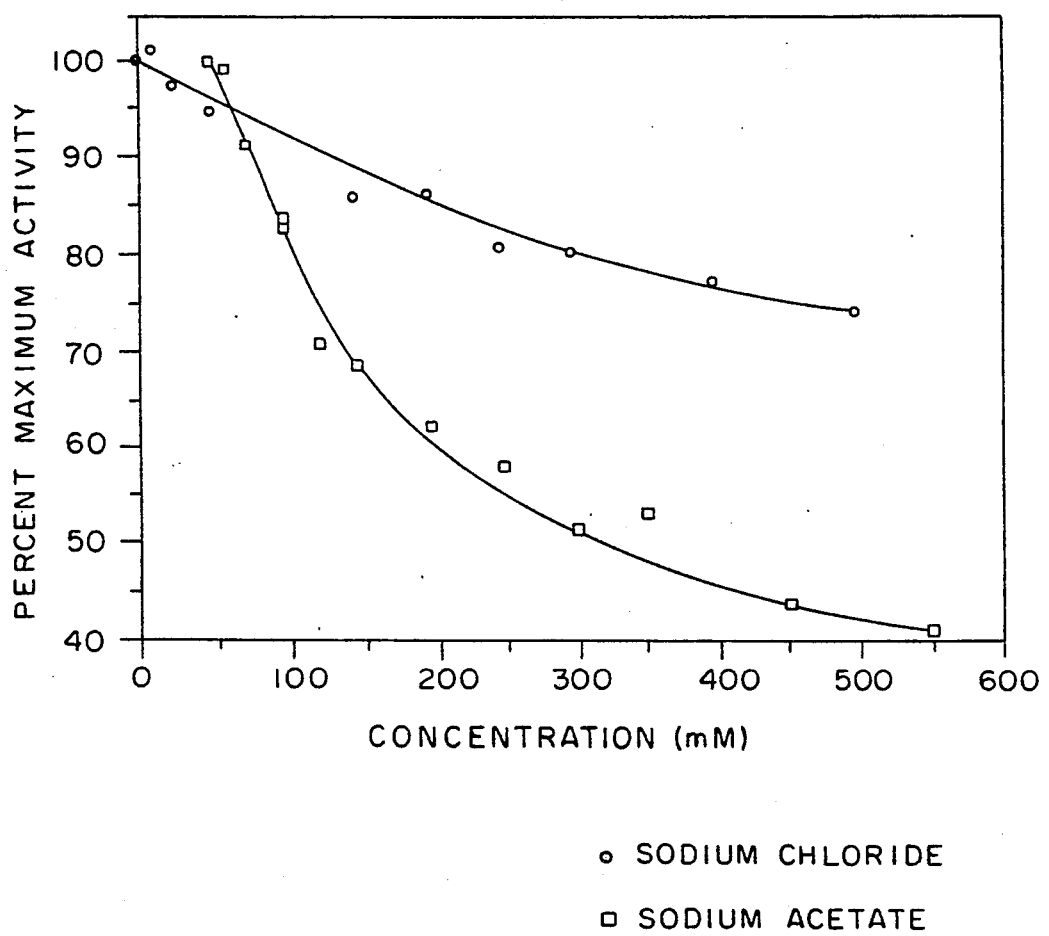
FIG. 4 depicts the inhibition of Acidothermus FP (filter paper) activity by inorganic and organic ions.

The inhibition of the filter paper (FP) activity by both inorganic and organic ions is shown in FIG. 4. In this figure the activity curve shown versus the concentration of salt is measured according to the IUPAc methodology discussed in Example 1, except that various amounts of a concentrated 1 M NaCl solution is added so that the final concentration of NaCl equaled that shown by the data points. The organic ion concentration is varied in a similar manner by the addition of 1 M acetate buffer (pH 5) up to the indicated concentrations. The observed filter paper activity decreased 25% in the presence of high concentrations of inorganic ions (salt). The observed filter paper activity is more sensitive to the presence of organic ions (acetate) as shown by the activity decreasing to 40% of maximum at acetate levels near 0.5 M.

EXAMPLE 6

Figure 5:
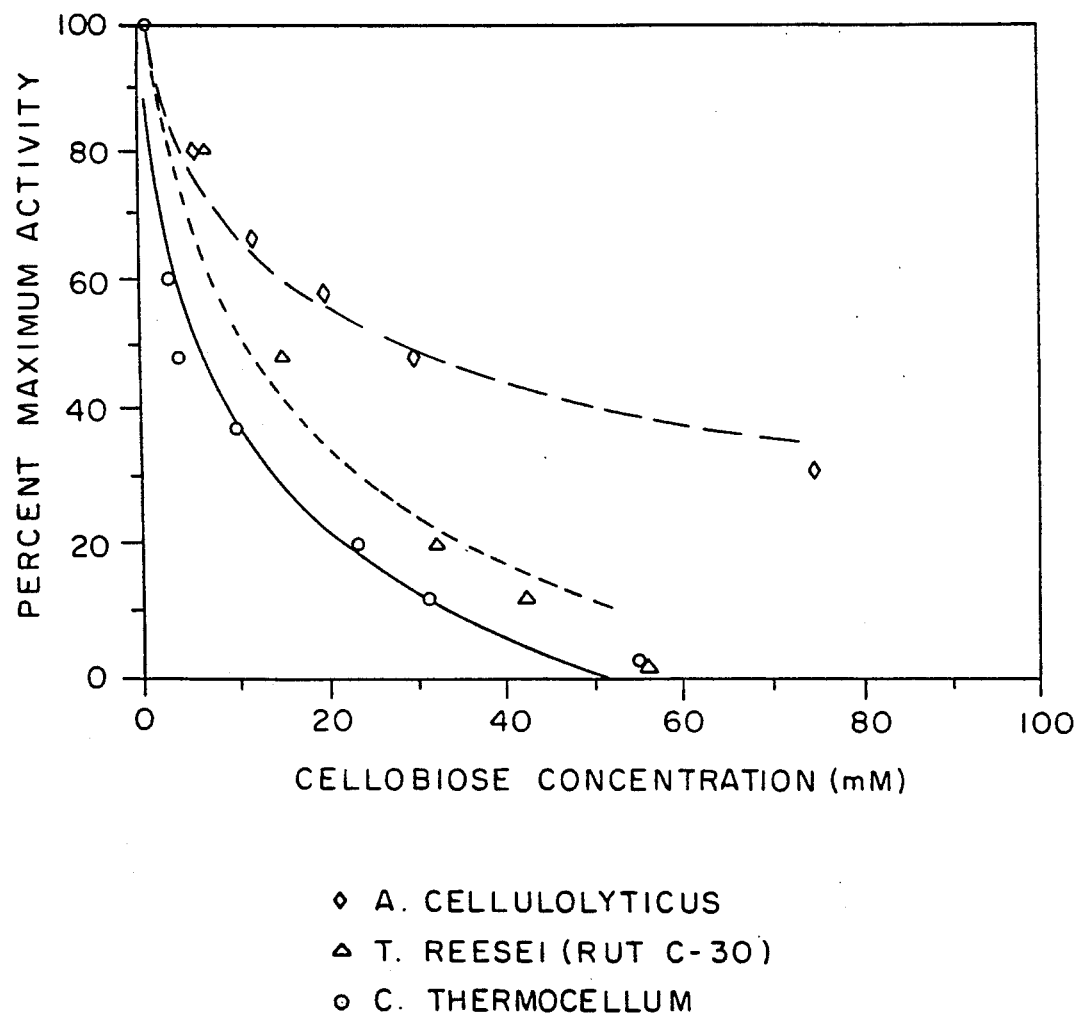
FIG. 5 depicts a comparison of the inhibition of the FP (filter paper) activity of *A. cellulolyticus* by the end-product, cellobiose, with *Trichoderma Reesei* (Rut C-30) and *Clostridium thermocellum*.

The inhibition of filter paper (FP) activity by the end product inhibitor cellobiose is shown in FIG. 5. Cellobiose is a potent inhibitor of the cellulases secreted by *Trichoderma reesei* with complete inhibition occuring at approximately 60 mM. The cellulase from *Acidothermus cellulolyticus* is much more resistant to inhibition by cellobiose with activity observed at levels near 0.5 M.

EXAMPLE 7

High Molecular Weight Endoglucanase

The high molecular weight endoglucanase is purified from the crude culture broth in the following sequence of steps. First, the crude culture broth from a 150 liter fermenter is centrifuged at 20,000 rpm in a CEPA continuous flow, bowl type centrifuge to remove the *Acidothermus cellulolyticus* microorganism. The supernatant recovered following centrifugation is concentrated greater than ten fold using an Amicon DC-30 ultrafiltration apparatus. Aliquots of the concentrated stock are further concentrated using a much smaller Amicon stirred cell ultrafiltration apparatus equipped with PM-10 membrane filters before loading onto a semi-preparative size exclusion chromotography (SEC) column. The SEC column is manufactured by Toyo Soda (TSK 3000 SWG) and measured 21.5 by 700 mm. The proteins elute from this column according to their molecular weight and are fractionated and collected as fractions of peaks. The molecular weight of these enzymes are found to range from about 156,600 to about 203,400 daltons.

The fractions containing the high molecular weight endoglucanase peak from this column are pooled and diafiltered against 15 mM Bis-Tris pH 6.5 ion exchange chromatography (IEC) loading buffer. The high molecular weight endoglucanase is then loaded onto a Pharmacia (Mono Q) IEC column.

Following washing with ten column volumes of loading buffer, the high molecular endoglucanase is eluted off the IEC using a shallow gradient of increasing ionic strength buffer that increases linearly from 0 to 50 mM in Nacl in 320 minutes at a flow rate of 1 ml per minute. The purified high molecular weight endoglucanase is eluted from this column at a gradient ionic strength corresponding to approximately 25 mM in NaCl.

The following diagram is a schematic representation of the purification protocol for the high molecular weight endoglucanase from *Acidothermus cellulolyticus*.

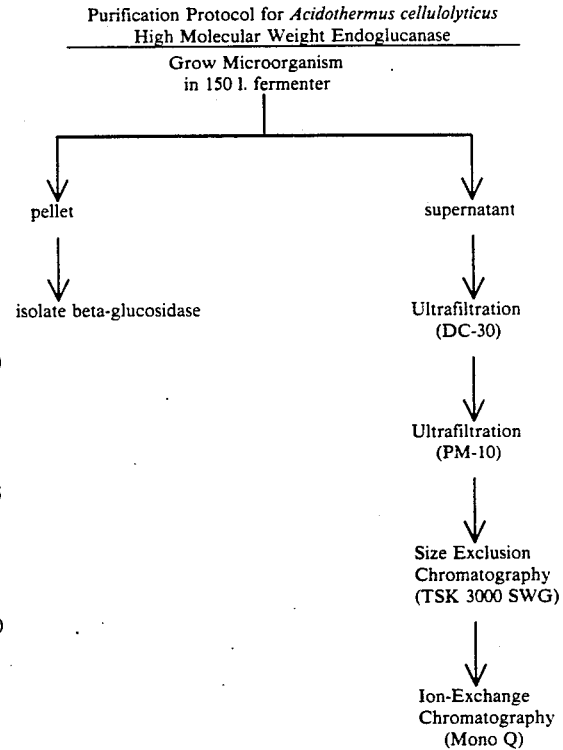

Purification Protocol for *Acidothermus cellulolyticus* High Molecular Weight Endoglucanase

EXAMPLES 8 and 9

The low molecular weight endoglucanases 1 and 11 are purified from the crude culture broth of a 150-liter fermentation in the following sequence of steps.

First, the crude culture broth from the 150 liter fermenter is centrifuged at 20,000 rpm in a CEPA continuous flow bowl type centrifuge to remove the *Acidothermus cellulolyticus* microorganism. The supernatant recovered following centrifugation is concentrated at least ten fold using an Amicon DC-30 ultrafiltration apparatus. Aliquots of the concentrated stock are further concentrated using a smaller Amicon stirred ultrafiltration apparatus equipped with a PM-10 membrane filter before loading onto a semi-preparative size exclusion chromatography (SEC) column. The low molecular weight endoglucanase peak eluting from the TSK 3000 SWG SEC column are fractionated with the activity pooled and ultraconcentrated to 10 ml. The ultraconcentrate is divided into six equal fractions to which 6.200 grams of CsC (ultrapure) is added to each. Concentrated acetate buffer (1 M, pH 5.0) is added (1.13 ml)

and the tubes are brought to 11.3 ml by adding water until the total weight added is 15.82 grams. Each of the six tubes are placed in a bucket in a Beckman SW-41 swinging bucket rotor and the loaded rotor placed in a Beckman ultracentrifuge. Following centrifugation for at least 96 hours at 35,000 rpm, the tubes are removed and fractionated. The isopycnic banded protein is pooled from the fractions obtained following centrifugation, diafiltered against loading buffer, and loaded onto an ion-exchange column. The Mono Q strong anion exchange column (Pharmacia) is equillbrated against 15 mM Bis-Tris pH 7.0 loading buffer before the diafiltered low molecular weight endoglucanase peak is loaded. Following washing with ten column volumes of loading buffer, the low molecular weight endoglucanase I and II are eluted from the column using a shallow gradient of increasing ionic strength buffer. The gradient increases linearly from 0 to 50 mM (Nacl concentration) in 320 minutes at a flow rate of 1 ml per minute. Low molecular weight endoglucanase I eluted from this column at a gradient ionic strength of approximately 25 mM while the low molecular weight endoglucanase 11 eluted at approximately 31 mM in NaCl. The pooled low molecular weight endoglucanase I and II peaks are subsequently ultraconcentrated and loaded separately onto the TSK 3000 SWG SEC column and fractionated. The fractions containing endoglucanase activity are pooled and ultraconcentrated (PM-lO) to obtain the final purified low molecular weight endoglucanases I and II, which have been found to have molecular weights respectively of between about 57,420 to 74,580 daltons and between about 50,000 to about 70,000 daltons.

The following diagram is a schematic representation of the purification protocol protocol for the low molecular weight endoglucanases I and II from *Acidothermus cellulolyticus*.

Purification Protocol for *Acidothermus cellulolyticus* Low Molecular Weight Endoglucanase

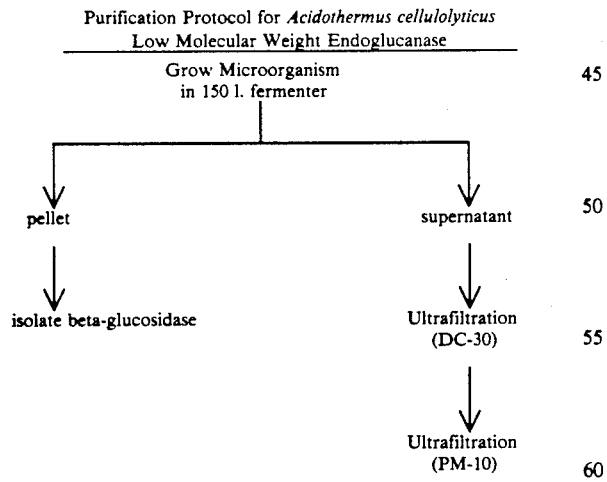

-continued
Purification Protocol for *Acidothermus cellulolyticus* Low Molecular Weight Endoglucanase

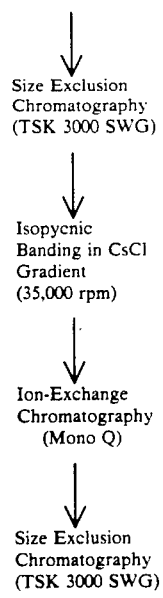

What is claimed is:

1. A substantially purified high molecular weight cellulase enzyme having a molecular weight of between about 156,600 to about 203,400 daltons from the bacterium *Acidothermus cellulolyticus* (ATCC 43068), said enzyme is water soluble, possesses both $C_I$ and $C_x$ types of enzyme activity, a high degree of stability toward heat, and exhibits optimum temperature for activity at about 65° C. at pH's from about 2 to about 9 and an inactivation temperature of about 90° C. at pH's from about 2 to about 9.

2. The purified cellulose enzyme of claim 1, wherein the pH for the optimum temperature activity is from about 4 to about 8, and the pH for the inactivation temperature is from about 4 to about 8.

3. The purified cellulase enzyme of claim 1, wherein the pH for the optimum temperature activity is about 5, and the pH for the inactivation temperature is about 5.

4. A method for the production of the enzyme of claim 1, comprising culturing said bacterium in a nutrient medium therefor, filtering crude cellulase enzyme complex by ultrafiltration, separating unpurified high molecular weight ultrafiltrate fractions by size exclusion chromotography, and loading said fractions on an anion ion exchange column equilibrated against about 15 mM Bis-Tris at about pH 6.5 loading buffer, washing said fractions with said loading buffer, and recovering said high molecular weight cellulase fractions by using a shallow gradient of an increasing ionic strength buffer that increases linearly from 0 to about 25 mM of NaCl, until purified high molecular weight cellulase fractions are eluted off.

* * * * *